United States Patent [19]
Del Bue et al.

[11] Patent Number: 5,334,531
[45] Date of Patent: Aug. 2, 1994

[54] PLASMID VECTOR FOR EXPRESSION IN BACILLUS AND USED FOR CLONING THE STRUCTURAL GENE WHICH CODES FOR THE HUMAN GROWTH HORMONE AND A METHOD OF PRODUCING THE HORMONE

[75] Inventors: Marina Del Bue; Paola Cosmina; Elisabetta Franchi, all of Milan; Guido Grandi, Segrate, all of Italy

[73] Assignee: Eniricerche S.p.A, Milan, Italy

[21] Appl. No.: 837,659

[22] Filed: Feb. 14, 1992

Related U.S. Application Data

[63] Continuation of Ser. No. 455,921, Dec. 21, 1989, abandoned, which is a continuation of Ser. No. 40,643, Apr. 21, 1987, abandoned.

[51] Int. Cl.$^5$ .................. C12N 1/21; C12N 15/18; C12N 15/75
[52] U.S. Cl. ................. 435/252.31; 435/320.1; 435/252.3; 435/69.1; 435/69.4; 435/172.3; 435/832; 435/839; 935/9; 935/13; 935/22; 935/29; 935/38; 935/56; 935/59; 935/60; 935/61; 935/74; 536/23.1; 536/23.5; 536/23.51; 536/24.1; 536/24.2
[58] Field of Search ............. 536/27, 23.1, 23.5, 536/23.51, 24.1, 24.2; 435/31, 172.3, 320.1, 172.1, 69.4, 252.3, 252.31, 252.5, 832, 839; 935/22, 23, 29, 9, 13, 38, 39, 40, 41, 56, 61, 45

[56] References Cited

U.S. PATENT DOCUMENTS

| | | | |
|---|---|---|---|
| 4,342,832 | 8/1982 | Goeddel et al. | 435/172.3 |
| 4,452,775 | 6/1984 | Kent | 424/42.5 |
| 4,626,510 | 12/1986 | Grandi | 435/320.1 |
| 4,760,025 | 7/1988 | Estell et al. | 435/222 |
| 4,987,078 | 1/1991 | Grandi et al. | 435/23.1 |

FOREIGN PATENT DOCUMENTS 0146901 7/1985 European Pat. Off.
2126590 3/1984 United Kingdom.

OTHER PUBLICATIONS

Grandi et al. (1986) New Plasmid Expression Vector for *Bacillus subtilis*. Plasmid 16, 1–14.
Honjo et al. (1986) Secretion of Human Growth Hormone in *Bacillus subtilis* Using Prepropeptide Coding Region of *Bacillus amyloliquifaciens* Neutral Protease Gene. J. Biotechnol. 4, 63–71.
Gentz et al. (1985) Promoters Recognized by *Escherichia coli* RNA Polymerase Selected by Fuction: Highly Efficient Promoters From Bactrio T5. J. Bacteriol. 164, 70–77.
Marina Del Bue et al., Plasmid Expression Vectors For B. Subtilis, Chimicaoggi, No. 3, Mar. 1987, pp. 73–75.
Herman A. DeBoer et al., A Hybrid Promoter and Portable Shine–Dalgarno Regions of *Escherichia coli*, Biochemical Soc. Symposis, vol. 48, 1983, pp. 233–244.
Donna M. Williams et al., Cloning Restriction Fragments That Promote Expression of a Gene in *Bacillus subtilis*, Jour. of Bacter., Jun. 1981, pp. 1162–1165.
Tomoko Tokunaga et al., Expression of a Synthetic Human Growth Hormone Gene in Yeast, Gene, 39, No. 1, 1985, pp. 117–120.
Charles P. Moran, Jr. et al., Nucleotide Sequences That Signal the Initiation of Transcription and Translation in *Bacillus subtilis*, Mol. Gen. Gene., vol. 186, 1982, pp. 339–346.
David V. Goeddel et al., Direct Expression in *Escherichia coli* of a DNA Sequence Coding for Human Growth Hormone, Nature, vol. 281, Oct. 18, 1979 pp. 544–548.

*Primary Examiner*—Christopher S. F. Low
*Attorney, Agent, or Firm*—Shea & Gould

[57] ABSTRACT

The description relates to a plasmid vector expression in Bacillus and used for cloning the structural gene which codes for the human growth hormone, a recombinant DNA molecule comprising plasmid vector and the structural gene of the human growth hormone and a method of preparing the hormone comprising inserting the recombinant DNA molecule into strains of Bacillus and cultivating the resulting transformed strains in a suitable culture environment and recovering the thus-synthesized hormone from the cells.

5 Claims, 4 Drawing Sheets

PLASMID VECTOR FOR EXPRESSION IN BACILLUS AND USED FOR CLONING THE STRUCTURAL GENE WHICH CODES FOR THE HUMAN GROWTH HORMONE AND A METHOD OF PRODUCING THE HORMONE

This application is a continuation of U.S. patent application Ser. No. 07/455,921, filed Dec. 21, 1989, now abandoned, which is a continuation of Ser. No. 07/040,643, filed Apr. 21, 1987, now abandoned.

The invention relates to a plasmid vector for expression in Bacillus and used for cloning structural gene which codes for the human growth hormone in strains of Bacillus, a recombinant DNA molecule comprising the cloning vector and the human growth hormone structural gene, and a microorganism transformed by the recombinant DNA molecule and capable of expressing the structural gene and high yields of the growth hormone.

The invention also relates to a method of preparing the human growth hormone comprising cultivating the transformed micro-organism in a suitable culture environment and recovering the thus-synthesized hormone from the cells.

The human growth hormone (hGH) is normally produced and secreted by the anterior lobe of the pituitary gland or adenohypophydsis during the entire life of the individual, and in higher quantities in the pre-adult period.

The hormone is produced in the form of a precursor (pre-hGH) comprising a secretion-signalling sequence on the aminoterminal part and the sequence of the mature hGH protein. During the secretion process the signal sequence is removed at the membrane and level the mature protein is secreted.

The growth hormone is made up of 191 amino acids and has a molecular weight of 21,500 Daltons.

Although its mechanism of action is not yet quite clear, it is known that hGH promotes skeletal growth, retention of nitrogen and protein synthesis and influences lipid and glucide metabolism.

A variety of clinical disorders due to hormonal deficiency have hitherto been treated with human growth hormone isolated from the hypophysis of dead bodies. However, the procedure for isolating and purifying the hormone is complex and expensive.

Furthermore, owing to the scarcity of the resulting hormone, treatment with hGH has been limited to the most serious cases, and therefore the need has been felt for alternative methods giving a good output of the hormone at reasonable cost.

Recent developments in the field of genetic engineering have made it possible to construct hybrid DNA molecules containing heterologous genes and to produce coding proteins for the structural genes by cultivating microorganisms transformed by the hybrid molecules.

The technical and patent literature describes numerous methods of producing human growth hormone by the recombinant DNA techniques.

British PA 2 055 982 relates to expression of semi-synthetic genes, more particularly the hGH gene, by constructing a hybrid plasmid vector and cultivating a strain of *E. coli* transformed by the hybrid plasmid vector.

European PA 20 147 describes and claims a vector for the human growth hormone and a strain of *E. coli* transformed by the vector. However, these known methods produce hGH by using vectors for expression in *E. coli*, a pathogenic gram-negative bacterium which normally lives in the human or animal intestinal tract.

In order to ferment the strains of transformed *E. coli* it is necessary to use culture systems which are controlled so as to avoid contamination and infection. This increases the cost of production.

From the industrial viewpoint, bacteria of the genus Bacillus are a preferable alternative to strains of *E. coli*.

The reason is that Bacillus bacteria are non-pathogenic, can easily be cultivated and have long been used in fermentative processes (Debabov "The Molecular Biology of the Bacilli" 1, 332 (1982) Dubnau, D.A. ed. Academic Press).

However, the use of Bacillus as host microorganism in the production of heterologous proteins has been restricted hitherto.

This is mainly due to the lack of cloning vectors for efficient expression of heterologous genes and high production of the coding proteins thereof.

A cloning vector has now been found which is capable of being maintained in stable manner in cells of Bacillus and can therefore obviate the problems of the known technique. To this end, one aim of the invention is a plasmid vector for expression in Bacillus and used for cloning the structural gene which codes for the human growth hormone.

Another aim of the invention is a molecule of recombinant DNA for expressing the human growth hormone in Bacillus, and obtained by joining the cloning vector to the nucleotide sequence which codes for the human growth hormone.

Another aim of the invention is a microorganism of the genus Bacillus transformed by the recombinant DNA molecule and capable of expressing the growth hormone structural gene and producing it with high yields.

A further aim of the invention is a method of preparing human growth hormone comprising cultivating the transformed microorganism in a suitable culture environment and recovering the synthesized hormone from the cells.

Other aims of the invention will be clear from the text of the description and the following examples.

According to the invention, the cloning vector was constructed from the vector pSM143 (ATCC53038) described in Italian PA 19960 A/85, by replacing the 750 base-pair (bp) XbaI-EcoRI fragment by a synthetic 73 bp fragment having the following sequence:

```
         —35                   —10
CTAGAAAAATTTATTTGCTTTCAGGAAAATTTTTCTGTATAATAGATTCA
    TTTTTAAATAAACGAAAGTCCTTTTAAAAAGACATATTATCTAAGT
          RBS
TAAATTTGAG AGCTCAAAGGAGG
ATTT AAACTC TCGAGTTTCCTCCTTAA
           ----
       SstI
```

The 73 bp fragment can be synthesized using any conventional technique and was constructed so as to obtain a promotor sequence and a ribosome recognition sequence (RBS), both sequences recognized by the RNA polymerase and Bacillus ribosomes and ensuring efficient expression of the structural gene of the human growth hormone placed under the control of the aforementioned sequences. More particularly the plasmid vector pSM143, the restriction map of which is shown in FIG. 1, was digested with restriction enzymes EcoRI and XbaI in a buffer solution at 37° C. for 1 hour.

The enzymatic reaction was then stopped by treating the reaction mixture with phenol-chloroform and chloroform-isoamyl, and the DNA was precipitated, separated and finally bonded to the 73 bp synthetic fragment. The bonding reaction was carried out in a buffer solution in the presence of T4 DNA ligase at a temperature of 14° C. for about 6 hours. The entire ligase mixture was then used to transform competent cells of E. coli, the transformed cells being selected on plates containing ampicillin.

Among the resulting positive clones (Amp$^R$), that clone was selected which contained the plasmid in which the 750 bp fragment EcoRI-XbaI had been substituted by the 73 bp synthetic fragment.

The plasmid, called pSM208, was then used to clone the structural gene which codes tot the human growth hormone and to construct the recombinant DNA molecule.

The structural gene of the growth hormone can be obtained either as described by Maniatis et al. (Molecular Cloning: A Laboratory Manual—p. 135, 140, 143—Cold Spring Harbor 1982) or by following one of the methods of synthesis in use (Oligonucleotides Synthesis-Practical Approach Series IRL Press) or finally by a semi-synthetic method as described by Goeddel et al (Nature, 281, p. 544 (1979)).

The method of preparing the gene does not limit the invention. According to the invention, therefore, the structural gene of hGH was prepared by a semi-synthetic method.

More particularly, the total RNA was isolated from human pituitary tissue, after which the mRNA (RNA polyadenylate) was separated by affinity chromatography on oligo (dT) cellulose from the total RNA (Edmonds et al. Proc. Natl. Acad. Sci USA, 68, p. 1336 (1971)). The resulting mRNA was then used to synthesize cDNA in the manner described by Maniatis et al. (Molecular Cloning: A Laboratory Manual—p. 217, Cold Spring Harbor 1982).

The resulting hypophysis cDNA molecules were then bonded to HindIII synthetic linkers (Biolabs) and inserted at the HindIII restriction site of plasmid pSR322. The resulting hybrid plasmids (pBR322-cDNA) were used to transform cells of E. coli selected for resistance to ampicillin.

The positive colonies were analyzed by the hybridization technique, using a DNA probe complementary with a region of the nucleotide sequence of the hGH gene, thus identifying the clones in which the hybrid plasmid comprises pSR322 and the cDNA the hGH gene. The cDNA of hGH was isolated from one of these plasmids and sub-cloned in the plasmid pUC9 (Boehringer) thus obtaining plasmid pWHA41 (FIG. 2).

Next, a HindIII linker was inserted in the plasmid pWHA41 at the end of the cDNA coding for hGH. More particularly, plasmid pWHA41 was cut by the SmaI restriction enzyme, precipitated and separated from the reaction mixture.

The resulting plasmid DNA was then bonded to the HindIII d(GAAGCTTC) synthetic linker in a buffer22 solution in the presence of T4 DNA ligase at a temperature of 23° C. for about 14 hours. The enzymatic reaction was then stopped by extracting the reaction mixture with a solution of phenol-chloroform and chloroform-isoamyl.

The plasmid DNA was then precipitated, separated and digested with the HindIII enzyme in a buffer solution.

The reaction was stopped by extraction with phenol-chloroform and chloroform-isoamyl and the DNA was precipitated.

The precipitate was then re-suspended in buffer solution in the presence of T4 DNA ligase and, after 14 hours at 14° C., the entire mixture of ligase was used to transform competent cells of E. coil JM101 (BRL). Positive colonies (Amp$^R$) were isolated from the resulting recombinants by selection on plates containing ampicillin, and the plasmid DNA was extracted therefrom and analyzed, It was found that the DNA from the aforementioned colonies contained the HindIII restriction site at the position of the SmaI site.

Enzymatic digestion of the plasmid resulted in two fragments, one containing about 680 base pairs and representing the structural gene of hGH. One of the positive clones was called JM101 (pSM209) and the plasmid DNA isolated therefrom (pSM209) was used to isolate the hGH gene from amino acid 17 to amino acid 191.

Plasmid DSM209 was cut by the FnuDII restriction enzymes, which cut at the level of the DNA between amino acid 16 and 17, and enzyme HindIII which cuts downstream of the stop codon (FIG. 2).

The digestion reaction was carried out by known general techniques and the 530 bp DNA fragment FnudII-HindIII containing the coding sequence for hGH 17-191 was separated from the reaction mixture by electrophoresis on acrylamide gel and eluted by the method of Maxam & Gilbert (Methods in Enzymology Vo. 65, p. 499–560 (1980)).

The complete sequence of the human growth hormone gene was then reconstituted by bonding the bp 530 Fragment to a 47 bp sequence which codes for the first 16 amino acids of the hGH and can result in the reconstruction of the FnuDII restriction sine. The 47 bp synthetic fragment, the sequence on which is given hereinafter:

TTCCCAACCATTCCCTTATCCAGGCTTTTTGACAACGCTATGCTCCG

AAGGGTTGGTAAGGGAATAGGTCCGAAAAACTGTTGCGATACGAGGC

FnuDII was phosphorylated before being bonded to the 510 bp fragment FnuDII-HindIII The ligase reaction, carried out in the presence T4 DNA ligase, was blocked by phenol-chloroform and chloroform-iso amyl and the DNA, after precipitation, was digested with HindIII enzyme.

The entire digestion mixture was then placed on acrylamide gel at 130 V for 3 hours, and the approximately 580 bp band containing the linear molecule made up of the linear fragment FnUDII-HindIII HindIII (530 bp) and the 47 bp synthetic fragment was electro-eluted.

The 47 bp sequence can be bonded to the FnudII-HindIII (530 bp) fragment in two orientations, only one of which leads to the reconstruction of the FnuDII restriction site and consequently to the formation of the complete structural gene human growth hormone.

The 580 bp fragment was cloned according the invention in plasmid pUC8, which had previously been digested with HindIII and EcoRI restriction enzymes and bonded to a synthetic fragment which on its end 3' contained the coding triplet for methionine, the sequence of which is RBS        met

AATTAAAGGAGGAATTCTTATG

TTTCCTCCTTAAGAATAC

————

EcoRI

This synthetic fragment can be bonded only to the EcoRI end of pUC8, owing to the presence at end 5' of the aforementioned plasmid in the complementary sequence.

The ligase reaction between plasmid pUC8 and the 580 bp fragment was carried out in the presence of T4 DNA ligase at a temperature of 14° C. for 6 hours.

After inactivation of the enzyme, the ligase mixture was used to transform competent cells of *E. coli* JM101 and the transforming substances were selected for ampicillin resistance.

The plasmid DNA was then extracted from the positive clones, digested with the EcoRI and HindIII enzymes and analyzed on agarose gel at 100 V for 2 hours.

Hybrid plasmids were found which contained a 590 bp fragment formed from the entire sequence of the structural gene of hGH and the methionine sequence. The exact orientation of the 47 bp sequence relative to the 530 pb fragment was then checked by the following method.

The hybrid plasmids obtained as described hereinbefore were digested with FnuDII enzyme at 37° C. for one hour and, after inactivation of the enzyme, the digestion mixture was placed on acrylamide Gel at 110 V for 3 hours. It was found that one of these plasmids, called pSM210, was cut by the enzyme FnuDII inside the structural gene of hGH, thus indicating the exact orientation of the 47 bp sequence relative to the 530 bp fragment.

According to the invention, the molecule of recombinant DNA was constructed by bonding the plasmid vector pSM208, previously cut by restriction enzymes, to the EcoRI-HindIII fragment of about 590 bp isolated from pSM210.

More particularly, plasmid pSM208 was successively cut with HindIII and EcoRI in buffer solution at 37° C.

The enzyme reaction was then stopped and the DNA was precipitated with ethanol and separated from the reaction mixture.

The DNA was then bonded to the EcoRI-HindIII fragment isolated from pSM210 in the presence of T4 DNA ligase, and the entire ligase mixture was then used to transform competent cells of Bacillus.

The following are examples of bacteria of the genus Bacillus which can be used as host microorganisms: *B. subtills, B. amyloliquefaciens, B. cereus* and *B. licheniformis*.

Among these, *Bacillus subtilis* (*B. subtilis*) is particularly preferred.

According to the invention, therefore, use was made of cells of *B. subtilis* SMS108 (NRRLB 15898) (his, leu, met, recE4, npr-) isolated in our laboratory. The *B. subtilis* cells were made competent by the method described by Contente and Dubnau (Mol. Gen. Genet. 167, 251–258 (1979)) and the transforming substances were selected for resistance to kanamycin. The positive clones were then examined by the method of rapid extraction of plasmid DNA and it was found that one of them contained hybrid plasmid pSM212 formed from pSM208 and from the 590 bp fragment containing the structural gene of hGH. The micro organism *B. subtilis* SMS108 (pSM212) was filed at the American Type Culture Collection Centre on 18.4.1986, No. ATCC 67098.

According to the invention, the strain *B. subtills* (pSM212) was cultivated in a liquid medium and, after cell lysis, the presence of a protein corresponding to the mature human growth hormone was detected in the lysed cells.

More particularly, the transformed bacterial strain was cultivated in VY medium (DIFCO) mixed with kanamycin, at a temperature of 30° to 40° C. for about 20 hours.

At the end of this time, the cell suspension was centrifuged and the cells were recovered, washed with buffer solution and finally lysed by known general methods.

The presence of the growth hormone was then determined in the lysed cells either by electroblotting (Towbin et al., PNAS, 1979, 76, 4350–4354) or by dyeing with Coomassie Blue ("Gel electrophoresis of proteins: A Practical Approach" ed. B. D. Homes and D. Rickwod—IRL Press Limited).

The results show the presence, in the lysed cells, of a protein having a molecular weight of 21,500 and comigrating with the natural hGH standard and making up 15 to 20% of the total proteins present. Also, as showed by analysis with immunoblotting, the protein reacts specifically with anti-hGH antibodies.

The quantity of hormone hGH produced from the strain of *B. subtills* SMS108 (pSM212) cultivated in an Erlenmayer flask was about 200 mg/ml per 6 g/l of cellular paste.

When cultivation was carried out in fermentation, quantities of hGH above 2 g/l were obtained.

The following experimental examples non-limitatively illustrate the invention.

EXAMPLE 1

Construction of pSM208Plasmid Vector

1 μg of plasmid pSM143 was digested with one unit of EcoRI and XbaI (Boehringer) restriction enzymes in 20 μl of buffer solution containing 50 mM Tris-HCl (pH 7.5), 100 mM NaCl and 10 mM MgCl₂ for 1 hour at 37° C. The enzyme reaction was stopped by extracting the reaction mixture with phenolchloroform, (1:1 V/V) and chloroform-isoamyl (24:1 V/V) and the DNA was precipitated by adding sodium acetate in a final concentration of 0.3 M and 2½ volumes of ethanol. The precipitate was separated by centrifuging and resuspended in 20 μl of buffer containing 66 mM Tris-HCl pH 7.6, 1 mM ATP, 10 mM MgCl₂ and 15 mM DTT and was bonded to 0.2 μg of the following synthetic fragment:

```
    =35=                        =10=
CTAGAAAAATTTATTTGCTTTCAGGAAAATTTTTCTGTATAATAGATTCA
    TTTTTAAATAAACGAAAGTCCTTTTAAAAAGACATATTATCTAAGT
        RBS
TAAATTTGAG AGCTCAAAGGAGG
ATTT AAACTC TCGAGTTTCCTCCTTAA
           -----
           SstI
``` in the presence of 1 unit of T4 DNA ligase, for 6 hours at 14° C. The reaction was inactivated at 70° C. for 10 minutes and used to transform cells of *E. coli* JM101 (BRL) made competent by the procedure described by Messing, Methods in Enzymology vol. 101, 20–78 (1983).

The transformed cells were selected for ampicillin resistance on LB (DIFCO) plates containing 50 ug/ml of ampicillin.

Figure 1:
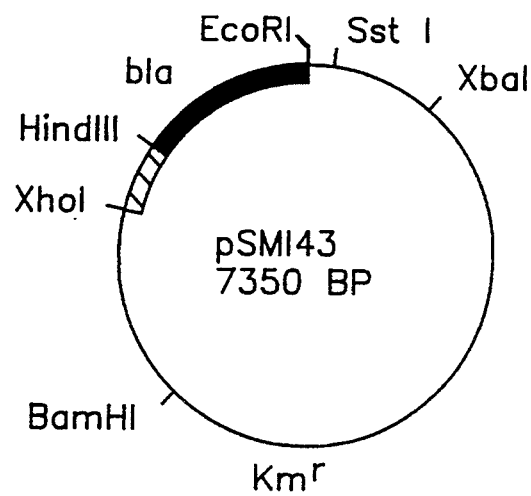
FIG. 1: Restriction maps of pSM143, pSM208 and pSM212.
Figure 1:
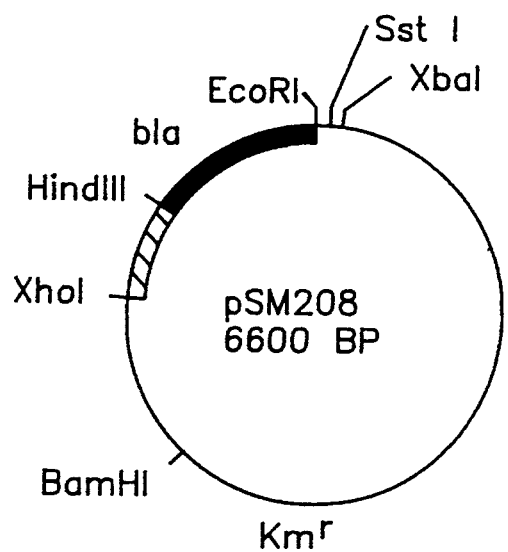
Figure 1:
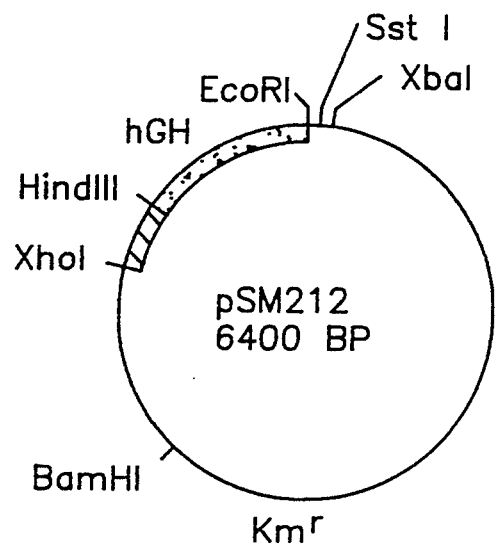

Plasmid pSM208, which was isolated from one of the ampicillin-resistant (Amp^R) colonies, had the map shown in FIG. 1, where the EcoRI-XbaI fragment of pSM143 has been substituted by the 73 bp synthetic fragment.

EXAMPLE 2

Insertion of the HindIII Site in Plasmid pWHA41

0.4 μg of plasmid pWHA41 was cut by one unit of SmaI (Boehringer) for 1 hour at 25° C. in 10 μl of buffer containing 15 mM Tris-HCl ( pH 8.5), 15 mM KCl, 6 mM MgCl₂ and 6 mM mercaptoethanol. The reaction was stopped by adding EDTA ( pH 8) up to a final concentration off 20 mM and extracting with phenolchloroform (1:1, (v/v)) and chloroform-isoamyl (24:1 (v/v) . The DNA was Precipitated by adding sodium acetate to the react ion mixture to a final concentration of 0.3 M and 2½ volumes of ethanol at a temperature off −80° C. for 15 minutes. After centrifuging in an Eppendorf centrifuge, model 5450 the precipitate was separated, dried in vacuo and resuspended in a buffer containing 66 mM Tris-HCl (pH 7.6) 1 mM ATP 1 mM spermidine 10 mM MgCl₂, 15 mM dithiothreitol (DTT) and 0.2 mg/ml of calf serum albumin (BSA).

1 μg of HindIII d(GAAGCTTC) (Boehringer) linker was phosphorylated in 10 μl of a buffer containing 66 nmM Tris-HCl pH 7.6, 1 mM ATP, 1 mM spermidine, 10 mM McCl₂, 15 mM DTT, 0.2 mg/ml BSA and 2 units of T4 DNA kinase (Biolabs) and incubated for 1 hour at 37° C. The reaction mixture was then added to 10 μl of the same solution containing pWHA41 cut with SmaI and incubated in the presence of 1 unit of T4 DNA ligase for 14 hours at 23° C. The reaction was stopped by adding 1 μl of a solution containing 0.5 M EDTA (pH 8) extracted once with phenol-chloroform and once with chloroform-isoamyl and precipitated with 2½ volumes of ethanol after adding sodium acetate to the solution up to a final concentration of 0.3 M. The solution was kept at 80° C. for 15 minutes and then centrifuged for 15 minutes. The thus-separated DNA was resuspended in 100 μl of a buffer containing 50 mM Tris-HCl pH 8, 10 mM MgCl₂, 50 mM NaCl and 20 units of HindIII (Boehringer) enzyme and incubated for 2 hours and 30 minutes at 37° C. The reaction was stooped by extraction with phenol-chloroform and chloroform-isoamyl and the DNA was precipitated by adding 2½ volumes of ethanol after adding sodium acetate to the solution up to a final concentration of 3 M. After centrifuging, the DNA was resuspended in 50 ml of a solution containing 10 mM Tris-HCl OH 8, 1 mM EDTA and 100 mM NaCl and placed on a Sephadex G50 (2 ml) column brought to equilibrium in the same buffer. The eluted DNA was precipitated as described hereinbefore and resuspended in 20 μl of a buffer containing 50 mM Tris-HCl OH 7.6, 10 m M MgCl₂, 10 mM DTT, 1 mM ATP and 1 unit of T4 DNA ligase (Boehringer) and incubated for 14 hours at 14° C. The reaction was inactivated for 10 minutes at 70° C. and then used (1 ng of DNA) to transform 0.3 ml of competent cells of *E. coli* JM101 (BRL). 12 white Amp$^R$ colonies were isolated from the recombinant substances, obtained by selection on LB (DIFCO) plates containing 50 μg/ml of ampicillin.

The 12 colonies were examined by rapid extraction of plasmid DNA by the method described by Rodriguez and Tait (in "Recombinant DNA Techniques: An Introduction" p. 50-51, Addison-Wesley Publishing Company). 1/20 of the resulting DNA was cut with one unit of HindIII restriction enzyme in 10 μl of the previously-described reaction mixture and incubated for 30 minutes at 37° C. After the enzyme had been inactivated at 70° C. for 10 minutes, the DNA was placed on 0.8% agarose gel and subjected to 100 V for 2 hours. All 12 colonies contained the HindIII restriction site at the position of the SmaI site. As expected, digestion of DNA resulted in two fragments, one of which contained about 690 base pairs and was the hGH gene.

One of the clones, called JM101 (pSM209) was chosen for further analysis and the plasmid DNA isolated therefrom, called pSM209, was extracted by the procedure described by Maniatis et al. (in Molecular Cloning, A Laboratory Manual—Cold Spring Harbor 1982).

EXAMPLE 3

3. Isolation of the hGH Structural Gene

Figure 2:
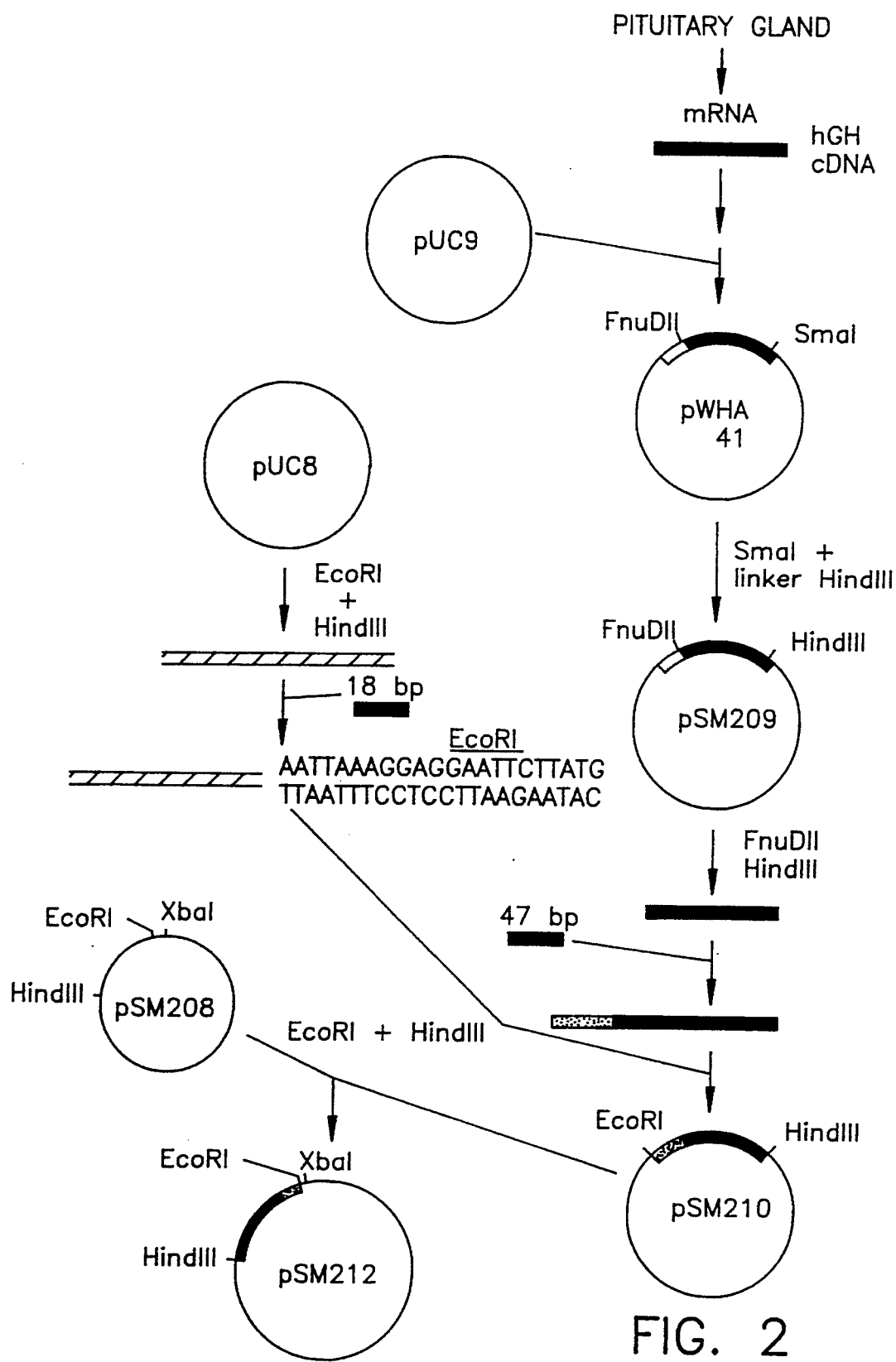
FIG. 2: Diagram of the transitions required for constructing plasmids pSM209, pSM210 and pSM212.

The DNA sequence which codes for the mature hormone from amino 17 to amino acid 191, was isolated from plasmid pSM209 by treatment with the restriction enzyme FnuDII (which cuts the DNA between aminoacid 16 and 17) and enzyme HindIII (which cuts downstream of the stop codon (FIG. 2)).

To this end, 50 μg of plasmid pSM209 were cut by 50 units of enzyme FnuDII (Biolabs) in 200 μl of reaction mixture containing 6 mH Tris-HCl pH 7.4, 6 mM NaCl, 6 mM MgCl₂ and 6 mM beta-mercapto-ethanol for 1 hour at 37° C. After the reaction had been inactivated at 70° C. for 10 minutes, the solution was brought to a concentration of 50 mM Tris-HCl pH 8, 10 mM MgCl₂ and 50 mM NaCl and incubated for a further hour at 37° C. in the presence of 50 units of HindIII (Boehringer) enzyme. The reaction was stopped by extraction with phenol-chloroform and chloroform-isoamyl and then, after adding sodium acetate to a final concentration of 0.3 M, the DNA was precipitated with 2½ volumes of ethanol. After incubation for 15 minutes at −80° C. and centrifuging for 15 minutes in an Eppendorf centrifuge, the precipitate was resuspended in 50 μl of TE (10 mM Tris-HCl pH 8 and 1 mM EDTA) and placed on 6% acrylamide gel. After the DNA had been separated by applying a voltage of 130 V for 3 hours, the approximately 530 bp band was eluted by the method described by Maxam and Gilbert (Methods in Enzymology Vol. 65 p. 499-540, 1980). The band contains the fragment having the coding sequence for hGH from aminoacid 17 to 191.

The complete sequence of the human growth hormone was reconstituted by using a synthetic 47 bp fragment which codes for the first 16 amino acid of hGH and can reconstitute the FnuDII site, the sequence of which is:

TTCCCAACCATTCCCTTATCCAGGCTTTTTGACAACGCTATGCTCCG

AAGGGTTGGTAAGGGAATAGGTCCGAAAAACTGTTGCGATACGAGGC

—FnuDII.

The two complementary 47-base DNA chains were synthesized by using a DNA Synthesizer SYSTEM ONE supplied by Beckman.

1.25 μg of the synthetic 47 bp fragment were phosphorylated in 20 μl of buffer containing 66 mM Tris-HCl pH 7.6, 1 1 ATP, 1 mM spermidine, 10 mM MgCl₂, 15 mM DTT, 0.2 mg/ml BSA and 2 units of T4 DNA kinase (Biolabs) for 1 hour at 37° C. The synthetic fragment was then bonded to 3 μg of the 530 bp fragment of DNA FnuDII-HindIII previously isolated from psM209, in 250 μl of the same buffer as used for the kinase reaction in the presence of 5 units of D4 TNA ligase (Boehringer). The reaction was carried out at 14° C. for 14 hours and the enzyme was inactivated by extraction with phenol-chloroform and chloroform-isoamyl and the DNA was precipitated from the aqueous phase after adding sodium acetate and ethanol as already described.

The precipitate was resuspended in 50 μl of buffer containing 50 mM Tris-HCl pH 8, 10 mM MgCl₂, and 50 mM NaCl and digested with 5 units of HindIII enzyme for 30 minutes at 37° C. The reaction was inactivated for 10 minutes at 70° C. and then placed on 6% acrylamide gel. After electrophoretic treatment (130 V for 3 hours) a band of approximately 580 pairs of bases was isolated and eluted and contained the linear molecule comprising the FnuDII-HindIII fragment and the synthetic 47 bp fragment. This molecule, in one of the two possible orientations in which the synthetic fragment can be bonded to the FnuDII-HindIII fragment, reconstitutes the entire structural gene of the growth hormone, and was cloned in *E.coli* plasmid pgC8 (BRL).

EXAMPLE 4

4. Cloning the Structural Gene of the Growth Hormone in pUC8

2.5 μg of plasmid pUC8 were digested with 2.5 units of HindIII for 50 minutes at 37° C. in a solution containing 50 mM Tris-HCl pH 8, 10 mM MgCl₂ and 50 mM NaCl. The enzyme reaction was inactivated 15 and then incubated for a further 30 minutes at 37° C. with 2.5 units of EcoRI after adding Tris-HCl and pH 8 up to a final concentration of 100 mM.

The reaction was inactivated with phenol-chloroform and the DNA, precipitated and separated, was resuspended in 50 μl of buffer containing 10 mM Tris-HCl pH 8, 1 mM EDTA and 1 mM of sodium perchlorate and re-precipitated by adding 25 μl of isopropanol. The pUC8 digested in this manner was then bonded to the synthetic DNA fragment having the following sequence:

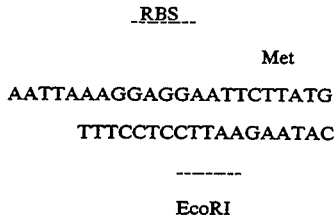

This fragment, which is synthesized by using a Beckman DNA synthesizer, can be bonded only to the EcoRI end of pUC8, owing to the presence of the complementary sequence at its 5' end.

0.185 μg of the synthetic fragment were bonded to 2.5 μg of pUC8 digested with EcoRI and HindIII as previously described, in 125 μl of a reaction mixture containing 66 mM Tris-HCl pH 7.6, 1 mM ATP, 1 mM spermidine, 10 mM MgCl$_2$, 15 mM DTT, 0.2 mg/ml BSA and 1 unit of T4 DNA ligase and incubated for 6 hours at 14° C. The reaction mixture, inactivated at 70° C. for 10 minutes, was mixed with 2 units of kinase and then incubated for a further hour at 37° C. The reaction was stopped by extraction with phenol-chloroform and chloroform-isoamyl and then, after adding 1/5 volumes of 5 M NaClO$_4$, the DNA was precipitated with 0.5 volumes of isopropanol. After centrifuging, the precipitate was resuspended in 25 μl of buffer containing 50 mM Tris-HCl pH 8, 10 mM MgC$_2$ and 50 mM NaCl and digested with 5 units of HindIII for 1 hour at 37° C. The reaction was stopped by extraction with phenol-chloroform and chloroform-isoamyl and the DNA was precipitated with sodium acetate and ethanol. 1 ug of the linear molecule of the E.coli plasmid pUC8, into which the synthetic fragment had been inserted as previously described was bonded to 0.8 μg of the linear molecule reconstituting the entire hGH structural gene, in 50 μl of a buffer containing 66 mM Tris-HCl pH 7.6, 1 mM ATP, 10 mM MgCl$_2$, 15 mM DTT and 1 unit of T4 DNA ligase for 6 hours at 14° C. After inactivation of the enzyme, the reaction mixture was used to transform competent cells of E. coli JM101.

Among the transforming substances competent cells of E. coli JM101 were obtained by selection on plates containing ampicillin (50 μg/ml) 12 white colonies (Amp$^R$) were analyzed by rapid extraction of the plasmid DNA. This procedure is for selecting those E. coli JM 101 cells containing the plasmid pSM 210 by using ampicillin which screens cloned cells from the others. 1/20 of the resulting DNA was digested with 1 unit of EcoRI and 1 unit of HindIII in 20 μl of a buffer containing 50 mM Tris-HCl pH 8, 10 mM MgCl$_2$ and 50 mM NaCl for 30 minutes at 37° C. The DNA was placed on 0.8% agarose gel and separated by applying a potential difference of 100 V for 2 hours. The plasmid DNA from the 12 colonies was shown to contain a 590 bp fragment comprising the 530 bp fragment, the synthetic sequence of 47 nucleotides, and the likewise synthetic sequence carrying the coding triplet for methionine.

In order to check the exact orientation of the 47 bp sequence relative to the 530 be fragment, 0.2 micrograms of plasmid DNA were cut with 1 unit of FnuDII enzyme in 20 μl of buffer containing 50 mM Tris-HCl pH 8, 10 mM MgCl$_2$ and 50 mM NaCl at 37° C. for 1 hour. After inactivation of the enzyme, the DNA was placed on 6% acrylamide gel and treated for 3 hours at 120 V. Five of the 12 plasmids were cut with FnuDII enzyme inside the hGH structural gene, thus showing the exact orientation of the synthetic 47 bp fragment with respect to the 530 bp fragment. One of these plasmids was called pSM210.

EXAMPLE 5

Cloning of hGH in pSM208

2 μg of plasmid pSM208 were digested with 2 units of HindIII for 30 minutes at 37° C. in a solution containing 50 mM Tris-HCl pH 8, 10 mM MgCl$_2$ and 50 mM NaCl. The reaction mixture was inactivated and then incubated for a further 30 minutes at 37° C. with 2 units of EcoRI after adding Tris-HCl pH 8, up to a final concentration of 100 mM. The reaction was stopped by extraction with phenol-chloroform and chloroform-isoamyl and the DNA was precipitated with ethanol.

3 μg of plasmid pSM210 were digested with the HindIII and EcoRI restriction enzymes by the method described for plasmid pSM208.

After precipitation μwith ethanol, the DNA was resuspended in 20 μl of TE and placed on 6% acrylamide gel. After electrophoretic treatment (130 V for 3 hours) the approximately 590 bp band containing the entire structural gene of hGH was isolated and eluted. 0.5 μg of the structural gene of hGH was bonded to 2 μg of plasmid pSM208 digested with EcoRI HindIII in 20 μl of reaction mixture containing 66 mM Tris-HCl pH 7.6, 1 mM ATP, 10 mM MgCl$_2$, 15 mM DTT and 1 unit of T4 DNA ligase for 14 hours at 14° C. 1 ug of the mixture was then used to convert cells of B. subtills SMS108 made competent as described by Contente and Dubnau (Mol. Gen. Genet. 167, 251-258, 1979).

The strain SMS108, constructed in our laboratories, was filed at the Northern Regional Research Centre (Peoria, Ill.), No. NRRL B-15898.

The transformed cells were selected on VY plates containing 5 μg/ml of kanamycin.

12 positive kanamycin resistant colonies were then examined by rapid extraction of the plasmid DNA. One of the colonies containing the hybrid plasmid with the fragment bearing the structural gene of hGH (pSM212) was called SMS108 (pSM212).

EXAMPLE 6

6. Expression of hGH in Bacillus subtills SMS108 (pSM212)

In order to check the expression of the hGH gene in the SMS108 (pSM212) strain of B. subtills, the strains were grown in a liquid medium and, after cell lysis, the presence of a protein corresponding to the mature growth hormone μgas found by immunoblot, (Towbin et al., PNAS, 1979, vol. 76 No. 9 p 4350-4354).

A culture of SMS108 (DSM212) was grown at 37° C. for 20 hours in VY medium (25 g/l DIFCO veal infusion broth, 5 g/l DIFCO yeast extract) containing kanamycin at a concentration of 5 μg/ml.

10 ml of the culture were centrifuged in a Sorvall centrifuge at 5 000 rpm for 10 minutes and the cells were washed twice with a buffer containing 30 mM Tris-HCl pH 7.5 and 50 mM NaCl and then resuspended in 10 ml of a solution containing 8 M urea, 1% SDS, 1% beta-mercaptoethanol and 62.5 mM Tris-HCl pH 6.8. The cells were lysed by using a French Pressure Cell (AMINCO) at 36000 Psi.

20 μl of the lysate were placed on 12.5% polyacrylamide STS gel (Laemmli, Nature, 1970, vol. 277, 680) and after electrophoretic treatment at 25 mA for 3 hours, the proteins were determined either with Coomassie Blue ("Gel electrophoresis of proteins: A practical approach" edited by B. D. Hames and D. Rickwod published by IRL Press Limited) or by transfer on to nitrocellulose filters (Schleicher & Schull, 45 μm pore size) (Towbin).

The presence of hGH was shown by treating the filters as described by Towbin, using rabbit anti-hGH antibodies (Miles) and rabbit anti-IgG goat antibodies conjugated with peroxidase (Miles).

Figure 3:
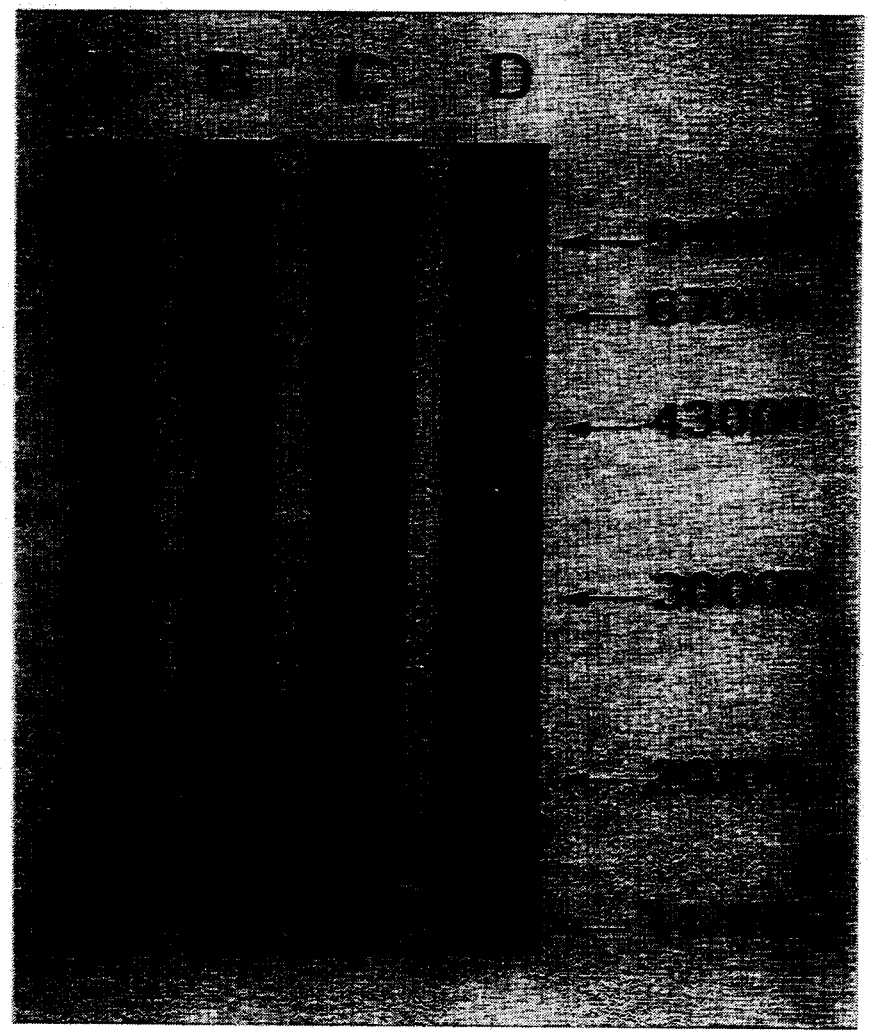
FIG. 3: Separation on SDS-acrylamide gel of the total proteins extracted from cells of *B. subtilis*. A: SMS108; B: SMS108(pSM212); C: natural hGH; D: molecular weight standards.

Dyeing with Coomassie Blue showed a protein having an apparent molecular weight of 21,500 and comigrating with the natural hGH standard (Calbiochem) and making up about 15–20% of the total proteins (FIG. 3).

Figure 4:
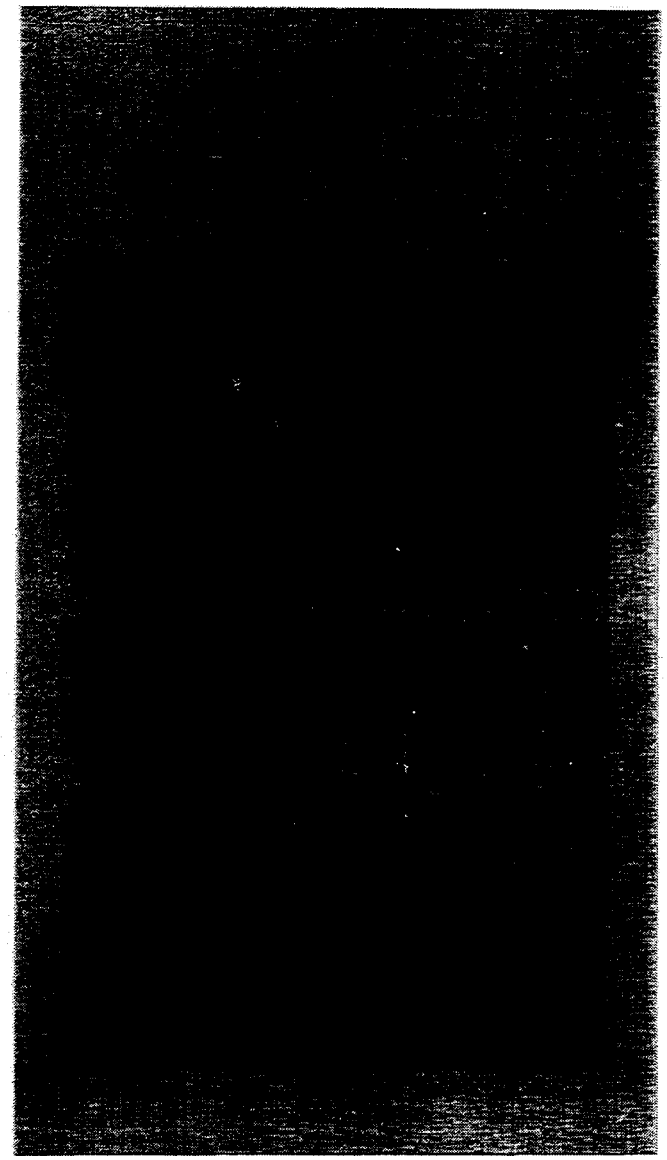
FIG. 4: Immunoblotting. A: SMS108; B: SMS108 (pSM212); C: natural hGH; D: molecular weight standards.

The protein reacts specifically with anti-hGH antibodies as demonstrated by immunoelectroblot analysis (FIG. 4). The quantity of hGH produced from the strain of B. subtilis SMS (pSMS212) was estimated at about 200 mg/l when fermentation was carried out in an Erlenmeyer flask under laboratory conditions (6 g of cell paste per litre of culture). When cultivation was brought about in a 10-litre fermenter, it was possible to obtain more than 2 grams of hGH per litre.

I claim:

1. A microorganism transformed with the plasmid pSM212 which is stably maintained and which expresses the structural gene encoding human growth hormone at greater than or equal to 200 mg/l of human growth hormone, wherein the microorganism is of the genus Bacillus.

2. A microorganism according to claim 1, wherein the microorganism is selected from the group consisting of *B. subtilis*, *B. amyloliquefaciens*, *B. cereus* and *B. licheniformis*.

3. The microorganism *B. subtilis* pSMS108 (pSM212) ATCC 67097.

4. A plasmid vector which is stably maintained in *Bacillus subtilis* for high level expression of the structural gene encoding human growth at greater than or equal to 200 mg/l of human growth hormone hormone, wherein said gene is under the control of the promoter region having the following sequence:

$$-35 \qquad\qquad -10$$

CTAGAAAAATTTATTTGCTTTCAGGAAAATTTTTCTGTATAATAGATTCA

TTTTTAAATAAACGAAAGTCCTTTTAAAAAGACATATTATCTAAGT

RBS

TAAATTTGAG AGCTCAAAGGAGG

ATTTAAACTC TCGAGTTTCCTCCTTAA

-----

SstI

5. The plasmid vector of claim 4 which is pSM212.

* * * * *

UNITED STATES PATENT AND TRADEMARK OFFICE
CERTIFICATE OF CORRECTION

PATENT NO. : 5,334,531
DATED : August 2, 1994
INVENTOR(S) : Del Bue et al.

It is certified that error appears in the above-indentified patent and that said Letters Patent is hereby corrected as shown below:

Title page :

Add [30] Foreign Application Priority Data

May 7, 1986         20345-A/86

Col. 14, line 16:
In Claim 4, in line 4, the word "hormone", second occurence should be deleted.

Signed and Sealed this

Twenty-eight Day of February, 1995

*Attest:*

BRUCE LEHMAN

*Attesting Officer*    *Commissioner of Patents and Trademarks*